US006627760B1

(12) United States Patent
Roberts

(10) Patent No.: US 6,627,760 B1
(45) Date of Patent: Sep. 30, 2003

(54) AMORPHOUS COMPOUND

(75) Inventor: Ronald John Roberts, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 261 days.

(21) Appl. No.: 09/891,190

(22) Filed: Jun. 25, 2001

(51) Int. Cl.$^7$ .................................. C07D 207/20

(52) U.S. Cl. ................ 548/533; 548/534; 548/535

(58) Field of Search ................ 548/533, 534, 548/535

(56) References Cited

U.S. PATENT DOCUMENTS

| | | | |
|---|---|---|---|
| 4,374,829 A | 2/1983 | Harris | 424/177 |
| 4,472,380 A | 9/1984 | Harris et al. | |
| 5,616,727 A | 4/1997 | Kottenhahn et al. | 548/533 |

FOREIGN PATENT DOCUMENTS

| | | |
|---|---|---|
| CA | 2285852 | 1/2000 |
| CA | 2285852 | 4/2001 |
| EP | 0168769 | 1/1986 |
| EP | 0738512 | 10/1996 |
| EP | 0943621 | 9/1999 |
| HU | 0207837 | 6/1993 |
| HU | 0214581 | 4/1998 |

OTHER PUBLICATIONS

Byrn, S. et al. *Pharmaceutical Solids: A Strategic Approach to Regulatory Considerations,* Pharmaceutical Research, vol. 12, No. 7, p. 945–954, 1995.
Grassi, M. et al. *Drug release from an ensemble of swellable crosslinked polymer particles,* Journal of Controlled Release vol. 68, p. 97–113, 2000.
Carli, F. et al. *Influence of polymer characteristics on drug loading into crospovidone,* Int. J. Pharm. vol. 33 (103), p. 115–124, 1986.
Habib, W. et al. *Fast–dissolve drug delivery systems,* Critical Reviews in Therapeutic Drug Carrier Systems, vol. 17(1), p. 61–72, 2000.
Wang et al. *Thermal Dependent Dehydration Process and Intramolecular Cyclization of Lisinopril Dihydrate in the Solid State.* Chem Pharm Bull 48(12) pp. 1890–1893 (2000).
Shimamoto et al. *Lisinopril Reverses Left Ventricular Hypertrophy Through Improved Aortic Compliance* 1996. J. of the American Heart Association, pp. 457–463.
Chaturvedi et al. *Effect of Lisinopril on Progression of Retinopathy in Normotensive People with Type I Diabetes.* Lancet vol. 351 (issue 9095) 1998, pp. 28–32.

Wong et al. *Determination of the Angiotensin–covering Enzyme Inhibitor Lisinopril in Urine Using Solid–Phase Extraction and Reversed–Phase High–Performance Liquid Chromatography.* Journal of Chromatography B, 673 (1995) pp. 306–310.
Chow et al. *Assessing the Treatment of Congestive Heart Failture: Diuretics, Vasodilators, and Angiotensin–Convertin Enzyme Inhibitors.* Pharmacotherapy 1993; 13 (5 pt 2) pp. 82S–87S.
Jugdutt et al. *Effect of Nitrates on Myocardial Remodeling after Acute Myocardial Infarction.* Am J Cardiol 1996; 77: pp. 17C–23C.
Ther Merck index. 1999. Monograph No. 5540, Lisinopril.
Ip et al. *Lisinopril,* from Analytical Profiles of Drug Substances and Excipients (Ed. Brihair, H. G.) Academic Press, vol. 21 pp. 233–276, (1992).
Blacklock et al. *Synthesis of Semisynthetic Dipeptides Using N–Carboxyanhydrides and Chiral Induction on Raney Nickel.* J. Org. Chem., vol. 53, No. 4, 1988. pp. 836–844.
Wu et al. Wu et al. *Synthesis of $N^2$–[(S)–1–Carboxy–3–phenylopropyl]–L–lysyl—proline (Lisinopril),* J. of pharmaceutical Pharm. Sci. vol. 74, No. 3, 1985, pp. 352–354.
Oparil et al. *Introduction–Treating the Older Hypertensive Patient.* Symposium on Prinivil. The American Journal of Medicine, pp. 1–6. Vol 85; (suppl. 3B) 1988.
Abrams et al. *Pathophysiology of Hypertension in Older Patients.* Symposium on Prinivil. The American Journal of Medicine, pp. 7–13. Vol 85; (suppl. 3B) 1988.
McDonald et al. *The Evolution of Current Hypertension Therapy.* Symposium on Prinivil. The American Journal of Medicine, pp. 14–18. vol. 85 (suppl. 3B) 1988.
Pool et al. *Clinical Experience and Rationale for Angiotensin–Converting Enzyme Inhibition with Lisinopril as the Initial Treatment for Hypertension in Older Patients.* Symposium on Prinivil. The American of Medicine, pp. 18–24. Vol 85; (suppl. 3B) 1988.
Beermann et al. *Pharmacokinetics of Lisinopril.* Symposium on Prinivil. The American Journal of Medicine pp. 25–30. Vol 85; (suppl. 3B) 1988.
Donohoe et al. *Lisinopril in the Treatment of Hypertensive Patients with Renal Impairment.* Symposium on Prinivil. The American Journal of Medicine, pp. 31–34. Vol 85; (suppl. 3B) 1988.

(List continued on next page.)

Primary Examiner—Paul J. Killos
(74) Attorney, Agent, or Firm—White & Case LLP

(57) ABSTRACT

The present invention relates to a novel form of (S)-1-[$N^2$-(1-carboxy-3-phenylpropyl]-L-lysyl]-L-proline known under the generic name lisinopril. Further, the present invention also relates to the use of the novel amorphous form of lisinopril for the treatment of hypertension and other cardiovascular diseases, pharmaceutical compositions containing it as well as processes for the preparation of the novel amorphous form of lisinopril.

22 Claims, 6 Drawing Sheets

OTHER PUBLICATIONS

Gomez et al. *Efficacy and Safety of Lisinopril in Older Patients with Essential Hypertension.* Symposium on Prinivil. The American Journal of Medicine pp. 35–37. Vol 85; (suppl. 3B) 1988.

Laher et al. *Antihypertensive and Renal Effects of Lisinopril in Older Patients with Hypertension.* Symposium on Prinivil. The American Journal of Medicine, pp. 38–43. Vol 85; (suppl. 3B) 1988.

Giles et al. *Lisinopril and Captopril in the Treatment of Heart Failure in Older Patients.* Symposium on Prinivil. The American Journal of Medicine, pp. 44–47. Vol 85; (suppl. 3B) 1988.

Lewis et al. *Lisinopril versus Placebo in Older Congestive Heart Failure Patients.* Symposium on Prinivil. The American Journal of Medicine, pp. 48–54. Vol 85; (suppl. 3B) 1988.

Rush et al. *Safety and Tolerability of Lisinopril in Older Hypertensive Patients.* Symposium on Prinivil. The American Journal of Medicine pp. 55–59. Vol 85; (suppl. 3B) 1988.

AMORPHOUS COMPOUND

FIELD OF THE INVENTION

The present invention relates to a novel amorphous form of (S)-1-[$N^2$-(1-carboxy-3-phenylpropyl]-L-lysyl]-L-proline. (S)-1-[$N^2$-(1-carboxy-3-phenylpropyl]-L-lysyl]-L-proline is known under the generic name lisinopril and its novel amorphous form is hereinafter referred to as amorphous lisinopril. Lisinopril has the tendency to readily form into a crystalline shape and no stable amorphous form has previously been reported. Further, the present invention also relates to the use of amorphous lisinopril in medical treatments, pharmaceutical compositions containing amorphous lisinopril, in particular 'fast melt' formulations, and processes for the preparation of amorphous lisinopril.

BACKGROUND OF THE INVENTION AND PRIOR ART

The compound (S)-1-[$N^2$-(1-carboxy-3-phenylpropyl]-L-lysyl]-L-proline, having the generic name lisinopril, as well as therapeutically acceptable salts thereof, are described in U.S. Pat. Ser. No. 4,374,829 (Merck & Co. Inc.), incorporated herein by reference. In said patent the compound is described in Example 119, and is referred to as N-α-[1(S)-1-carboxy-3-phenylpropyl]-L-lysyl]-L-proline. Lisinopril is a drug on which extensive clinical experience has been obtained. It is currently sold under the trademark ZESTRIL® or PRINIVL®.

Lisinopril is a peptidyl dipeptidase inhibitor useful in treating cardiovascular diseases and disorders, such as hypertension and congestive heart failure (CHF) in mammals and especially in man. It inhibits the angiotensin converting enzyme (ACE) that catalyses the conversion of angiotensin I to the vasoconstrictor peptide, angiotensin II. Angiotensin II also stimulates aldosterone secretion by the adrenal cortex. Inhibition of ACE results in decreased concentrations of angiotensin II which results in decreased vasopressor activity and reduced aldosterone secretion.

ACE is known to be present in the endothelium and increased ACE activity in diabetic patients which results in the formation of angiotensin II and destruction of bradykinin, potentiates the damage to the endothelium caused by hyperglycaemia. ACE inhibitors, including lisinopril, inhibit the formation of angiotensin II and breakdown of bradykinin and hence ameliorate endothelial dysfunction.

In terms of the pharmacokinetic properties of lisinopril, following oral administration, peak serum concentrations occur within about 7 hours, although there is a trend to a small delay in time taken to reach peak serum concentrations in acute myocardial infarction patients. On multiple dosing lisinopril has an effective half-life of accumulation of about 12.6 hours. Declining serum concentrations exhibit a prolonged terminal phase, which does not contribute to drug accumulation. This terminal phase probably represents saturable binding to ACE and is not proportional to dose. Based on urinary recovery, the mean extent of absorption of lisinopril is approximately 25%, with interpatient variability (6–60%) at all doses tested (5–80 mg). Lisinopril does not undergo metabolism and absorbed drug is excreted unchanged entirely in the urine.

It has been reported previously that amorphous forms of certain drugs exhibit distinct dissolution characteristics and in some cases distinct bioavailability patterns compared to the crystalline form (see Konno T, (1990) Chem. Pharm. Bull. 38:2003–2007). The dissolution rate may favor one formulation over another. For some therapeutic indications, one formulation may be favored over another. Similarly one formulation may be more suitable for treating certain patient populations. Therefore it is desirable to have a procedure for making amorphous product or for converting a crystalline form of the drug to the amorphous form.

In addition, it is often desirable to make 'fast melt' tablet formulations of certain drugs.

DESCRIPTION OF THE INVENTION

It has surprisingly been found that the substance lisinopril can be prepared in a stable amorphous form. Moreover, it has been found that amorphous lisinopril possesses far greater solubility than the crystalline form. Such a more soluble form of lisinopril may render the product more suitable to certain formulations where quick solubility is desired, such as 'fast melt' (melt on the tongue type) formulations. It is an object of the present invention to provide amorphous lisinopril. It is a further object of the invention to provide mixtures of amorphous lisinopril with other solid forms of lisinopril, such as crystalline lisinopril. Another object of the present invention is to provide a process for the preparation of amorphous lisinopril, substantially free from other forms of lisinopril. Additionally it is an object of the present invention to provide pharmaceutical formulations comprising amorphous lisinopril.

Although crystalline lisinopril has been in the public domain for some time now, the Applicants are not aware of any disclosure of amorphous lisinopril having been made and publicly disclosed. Indeed, it was generally regarded that amorphous lisinopril would be difficult to make, particularly in a stable form. Applicants' previous attempts at crystallization to produce other forms, always generated crystalline hydrates or solvates that quickly took up water reverting to the crystalline form. No amorphous product was ever formed.

Amorphous lisinopril is a non-crystalline, 'porous particulate' form exhibiting advantageous properties, such as being more soluble than crystalline lisinopril. In addition, the amorphous lisinopril particles are glassy in appearance having smooth surfaces with characteristic porous rounded holes with the absence of regular faces present in crystalline materials. Particles can range from small (1–10 μm) to larger particles (500 μm) in addition to aggregated particles, which are granular in appearance. The granular shape of the amorphous particles will impart improved flow characteristics and so aid tablet manufacture compared to the needle-like structures found in the crystalline material. ZESTRIL® is conventionally manufactured using wet granulation and tabletting.

Tablet manufacture by direct compression, as opposed to wet granulation, is prone to segregation of the drug substance from the remaining excipients, leading to a non-uniform mix. This gives rise to tablets of variable drug content. Segregation is exacerbated by wide differences in the particle size of the drug substance and the excipients. The larger particle size of the amorphous lisinopril compared to the crystalline material would be closer to that of the excipients typically used in direct compression formulations and so would minimise segregation. Further, it is well known that amorphous materials posses improved compression characteristics over the crystalline form. For example, commercial grades of lactose are produced by a spray drying technique to introduce some amorphous content which improves the compression force/hardness profile of the excipient (*Handbook of Pharmaceutical Excipients*, 3rd Edition, A. H. Kibbe, Pharmaceutical Press, p. 276). The particle size and shape of amorphous lisinopril may thus make it more suitable for direct compaction tabletting.

Thus, according to a first aspect of the invention there is provided lisinopril in amorphous form.

There is also provided (S)-1-[$N^2$-(1-carboxy-3-phenylpropyl]-L-lysyl]-L-proline, or a pharmaceutically-acceptable salt thereof in amorphous form.

Amorphous materials do not exhibit the three-dimensional long-range order found in crystalline materials but are structurally more similar to liquids where the arrangement of molecules is random. Amorphous solids are not crystalline and therefore do not give a definitive x-ray diffraction pattern, in addition they do not give rise to a melting point and tend to liquify at some point beyond the glass transition point (Hancock and Zografi, (1997) J. Pharm. Sci., 86:1–12).

The preferred method of differentiating amorphous lisinopril from other crystalline and non-crystalline forms of lisinopril is X-ray powder diffraction (XRPD). The XRPD pattern of pure amorphous lisinopril, as illustrated in FIG. 1, can be seen to lack discernible acute peaks. Thus, amorphous lisinopril, according to the present invention, is characterized in providing an X-ray powder diffraction pattern containing one or more broad diffuse halos having very low counts (i.e. see FIG. 1) in contrast to the sharp diffraction peaks characteristic of crystalline materials (i.e. see FIG. 2). Of course it will be appreciated that a mixture comprising detectable amounts of both crystalline and amorphous lisinopril will exhibit both the characteristic sharp peaks and the diffuse halo(s) on XRPD. This will be evident by an increase in the baseline and also a reduction in crystalline peak intensities.

Thus, according to a further aspect of the invention there is provided amorphous lisinopril characterized in providing an X-ray powder diffraction pattern containing one or more broad diffuse halos, and preferably having very low counts (lacking any discernible peaks).

The term "broad diffuse halo" is the art recognized term for the 'humps' observed in XRPD (see Klug and Alexander, *X-ray diffraction procedures: for polycrystalline and amorphous materials*, 2nd edition, 1974, John Wiley and Sons, pp791–792).

In a preferred embodiment the amorphous form is stable.

The term stable as used herein, refers to the tendency to remain substantially in the same physical form for at least a month, preferably at least 6 months, more preferably at least a year, still more preferably at least 3 years, even still more preferably at least 5 years, when stored under ambient conditions (25° C./60%RH) without external treatment. As noted above amorphous forms of many compounds often revert to the crystalline form in a relatively short time period (days/weeks rather than months/years). Substantially the same physical form in this context means that at least 70%, preferably at least 80% and more preferably at least 90% of the amorphous form remains. The glass transition point of a compound is a measure of the physical stability to crystallization.

In a preferred embodiment the amorphous lisinopril has in increasing order of preference a glass transition point (Tg), measured by Differential Scanning Calorimetry (DSC) or Thermal Mechanical Analysis (TMA), greater than 70° C., 80° C., 90° C., 100° C.,120° C., 130° C., 140° C.and 160° C. It is generally regarded that as a rough rule of thumb a Tg of 50° C. or greater above the storage temperature should assure reasonable physical stability to crystallization. In a preferred embodiment the amorphous lisinopril according to the invention has, when dry, a glass transition point (Tg) measured by Thermal Mechanical Analysis (TMA) of 100° C. or more, more preferably of 120° C. or more.

Thus, according to a further aspect of the invention there is provided amorphous lisinopril which is (S)-1-[$N^2$-(1-carboxy-3-phenylpropyl]-L-lysyl]-L-proline, or amorphous salts thereof, providing an X-ray powder diffraction pattern containing one or more broad diffuse halos having very low counts, and possessing, when dry, a glass transition point (Tg) measured by Thermal Mechanical Analysis (TMA) of at least 100° C.

Amorphous lisinopril, or the presence of some amorphous lisinopril, can be distinguished from crystalline lisinopril, using X-ray powder diffraction, Raman spectroscopy, solution calorimetry, differential scanning calorimetry, solid state nuclear magnetic resonance spectra (ssNMR) or infrared spectroscopy. Each of these techniques is well established in the art. Amorphous lisinopril can also be identified based on the morphology of the particles seen under an electron microscope. Furthermore, amorphous lisinopril is much more soluble than crystalline lisinopril, providing another means of discriminating between the crystalline and amorphous lisinopril forms, or detecting an amount of amorphous form within a lisinopril preparation.

As noted above, the preferred method of differentiating amorphous lisinopril from other crystalline and non-crystalline forms of lisinopril is X-ray powder diffraction (XRPD).

Another method of distinguishing physical forms, such as crystalline and amorphous lisinopril, is $^{13}$C Solid state NMR spectra (ssNMR) acquired with cross polarization, magic angle spinning and high power proton decoupling. The isotropic chemical shifts (peak positions) measured in solid state NMR spectra are not only a function of the molecule's atomic connectivity, but also of molecular conformation and inter- and intra-molecular interactions. Thus different peak positions may be observed for different physical forms. For amorphous materials, the dispersion of environments often causes substantially broadened spectra (*Nuclear Magnetic resonance Spectroscopy*, R K Harris, Longman 1987), p. 155.).

The $^{13}$C solid state NMR spectra of amorphous lisinopril, as illustrated in FIG. 4, can be seen to give broadened peaks. Thus, amorphous lisinopril, according to the present invention, is characterised in providing a $^{13}$C solid state NMR spectra containing broadened peaks (as in FIG. 4) in contrast to the sharp, well defined peaks characteristic of crystalline materials (as in FIG. 5).

In one embodiment, the amorphous lisinopril of the present invention is substantially free from other forms of lisinopril. Substantially free from other forms of lisinopril shall be understood to mean that amorphous lisinopril contains less than 50%, preferably less than 25%, more preferably less than 10% and still more preferably less than 5% of any other forms of lisinopril, e.g. crystalline lisinopril.

It will be appreciated however, that because of the enhanced solubility property of amorphous lisinopril, mixtures comprising substantially crystalline or other solid forms of lisinopril with amorphous lisinopril will, depending on the amount of amorphous product present, may also possess varying degrees of increased solubility. Such mixtures comprising amorphous lisinopril can be prepared, for example, by mixing amorphous lisinopril prepared according to.the present invention with other solid forms of lisinopril, such as crystalline form, prepared according to prior art methods. A mixture might also be prepared if the manufacturing process is incomplete, or incorporates steps that allow or cause amorphous product to be formed.

Thus, the present invention also relates to mixtures comprising amorphous lisinopril in admixture with other solid forms of lisinopril. Such mixtures comprising amorphous lisinopril include for instance mixtures containing a detectable amount of amorphous lisinopril, 1%, 2%, 5%, 10%, 20%, 30%, 40%, 50%, 60%, 70%, 80%, 90%, 95%, 98%, or 99% (by weight), of amorphous lisinopril.

Examples of other solid forms of lisinopril include, but are not limited to, crystalline lisinopril, and other polymorphs.

A detectable amount of amorphous lisinopril is an amount that can be detected using conventional techniques, such as FT-IR, Raman spectroscopy, XRPD, TMA, DSC and the like.

Numerous techniques can be employed to detect a particular form of a compound within a mixture. The limits of detection of a particular form in admixture with another form, i.e. crystalline in amorphous or vice versa, is as follows: by XRPD it is reported to be approximately 5% according to Hancock and Zografi (J. Pharm. Sci., 86:1–12, 1997) and approximately 2.0% according to Surana and Suryanarayanan (Powder Diffraction, 15:2–6, 2000). The limits of detection by solution calorimetry is reported to be approximately 1% according Hogan and Buckton (International Journal of Pharmaceutics, 207:57–64, 2000). The limits of detection by solid state NMR is reported to be approximately 5–10% according to Saindonet al., (Pharmaceutical Research, 10:197–203,1993). The limits of detection by near infra red spectroscopy is reported to be approximately 2–5% according to Blanco and Villar (Analyst, 125:2311–2314, 2000). The limits of detection by Modulated Differential Scanning Calorimetry (MDSC) is reported to be approximately 6% according to Saklatvala et al., (International Journal of Pharmaceutics, 192:55–62, 1999). The limits of detection by FTRaman spectroscopy is reported to be approximately 2% according to Taylor and Zografi (Pharm. Res. 15:755–761, 1998).

Amorphous lisinopril can be prepared by precipitation. Other ways of making amorphous product include: spray drying, freeze drying (lyophilisation), melt precipitation, vapour condensation, crash cooling, from supercritical fluids e.g. using Solution Enhanced Dispersion by Supercritical fluids (SEDS), Rapid Expansion of Supercritical Solution (RESS) processes etc, co-precipitation with suitable excipients (these include sugars, acids, polymers, insoluble or enteric polymers, surfactants) to form solid dispersions, molecular dispersions, co-precipitates or co-evaporates by melting or fusion, or from solvents, including supercritical solvents.

The preferred method of preparing amorphous lisinopril is by precipitation using an anti-solvent. Thus, amorphous lisinopril may be prepared by dissolving any form of lisinopril in a suitable solvent, such as for instance water or methanol, followed either by (i) precipitation via addition of a suitable antisolvent which is miscible with the first solvent, such as for example acetone when the first solvent is methanol, or (ii) addition of an immiscible antisolvent, such as for example toluene or chlorobenzene when the first solvent is water, and azeotroping to allow precipitation of amorphous lisinopril.

According to one aspect of the invention there is provided a process for the preparation of amorphous lisinopril comprising the steps of:

a) dissolving or suspending lisinopril of any form, or a mixture of lisinopril of any form in a suitable solvent;
b) adding an antisolvent to precipitate out amorphous lisinopril; and,
c) isolating the amorphous lisinopril thus obtained.

In one embodiment the solvent and antisolvent are immiscible and precipitation of the morphous product in step b) is effected following evaporation of the immiscible solution.

Thus, the process comprises the steps of:

a) dissolving or suspending lisinopril of any form, or a mixture of lisinopril of any form in a suitable solvent;
b) adding an antisolvent which is immiscible with the solvent used in step a);
c) azeotroping to precipitate out amorphous lisinopril; and,
d) isolating the amorphous lisinopril thus obtained.

By the term 'any form' we include, solvated and desolvated forms, crystalline forms and other non-crystalline forms.

In one embodiment the lisinopril is dissolved in the solvent in dehydrated form. In such instances, it is preferred that the dehydrated lisinopril is added to the solvent before the lisinopril has had a chance to rehydrate. It is preferred therefore, that the dehydrated lisinopril is prepared by heating a hydrated form for a suitable length of time and the 'still hot' dehydrate is added directly to the solvent mixture. Equally, in an alternate embodiment, the solvent can be added to the lisinopril dehydrate.

The inventors have found that it is not necessary to dehydrate lisinopril dihydrate in every case. However, if hydrated lisinopril is dissolved in water as the solvent it is preferred that non-polar antisolvents are used. When using dehydrated lisinopril it is preferred that polar antisolvents are used, however non-polar antisolvents can also be used.

It is preferred that the temperature of the mixture during mixing with the antisolvent is 0 to +50° C., most preferably +20° C. to 40° C., and for the antisolvent to be at ambient temperature before mixing. It is preferred to add the antisolvent to the lisinopril solvent solution. The antisolvent may be added continuously or discontinuously, preferably discontinuously in two or more aliquots over a period of up to, but not limited to 8 hours. The amount of antisolvent should be such that the concentration of lisinopril in the resulting mixture is higher than the solubility. The preferred ratio of antisolvent to lisinopril solvent solution should be in the range of 5:1 to 10:1 by volume. The water content in the final mixture should preferably be below 10% by volume. Mixing, e.g. agitation or stirring, is preferable both during the dissolving step and the precipitation step. The precipitation should continue for a period to ensure that amorphous product formation is as complete as possible, e.g. up to 15 hours, preferably, 1–8 hours.

The amorphous product may be separated from the solution, e.g. by filtration or centrifugation, followed by washing with a wash solution, preferably a solvent in which amorphous lisinopril has a very low solubility. The amorphous product can be dried to a constant weight, e.g. at +30° C. to +50° C., preferably at reduced pressure, for, e.g. 10 to 48 hours.

For storage, the amorphous product is preferably kept at 25° C., 60%RH (ambient conditions) having a water content up to about 30% (for relative humidities in the range 40% RH–80% RH). In a preferred embodiment the water content is from between about 5% and 20%, more preferably between about 7% and 18%.

The invention is therefore also directed to a method of enhancing the bioavailability of lisinopril, particularly crystalline lisinopril dihydrate, comprising admixing said lisinopril with amorphous lisinopril. Alternatively, the method comprises converting any amount of lisinopril, particularly crystalline lisinopril, to amorphous lisinopril.

In a further aspect, the invention provides a compound obtainable by a process or method as described above.

'Zestril' has received regulatory approval for use in the following indications:

Hypertension

'Zestril' is indicated in the treatment of essential hypertension and in renovascular hypertension. It may be used alone or concomitantly with other classes of antihypertensive agents.

Congestive Heart Failure

'Zestril' is indicated in the management of congestive heart failure as an adjunctive treatment with diuretics and, where appropriate, digitalis. High doses reduce the risk of the combined outcomes of mortality and hospitalization.

Acute Myocardial Infarction

'Zestril' is indicated for the treatment of haemodynamically stable patients within 24 hours of an acute myocardial infarction, to prevent the subsequent development of left ventricular dysfunction or heart failure and to improve survival. Patients should receive, as appropriate, the standard recommended treatments such as thrombolytics, aspirin and beta-blockers.

Renal and Retinal Complications of Diabetes Mellitus

In normotensive insulin-dependent and hypertensive non-insulin-dependent diabetes mellitus patients who have incipient nephropathy characterised by microalbuminuria, 'Zestril' reduces urinary albumin excretion rate. 'Zestril' reduces the risk of progression of retinopathy in normotensive insulin-dependent diabetes mellitus patients.

According to the invention there is further provided a pharmaceutical composition comprising amorphous lisinopril, as active ingredient, in association with a pharmaceutically acceptable carrier, diluent or excipient and optionally other therapeutic ingredients. Compositions comprising other therapeutic ingredients are especially of interest in the treatment of hypertension, congestive heart failure, acute myocardial infarction and in renal and retinal complications of diabetes mellitus.

The invention also provides the use of amorphous lisinopril in the manufacture of a medicament for use in the treatment of a cardiovascular related condition, and in particular, a method of treating a hypertensive or congestive heart failure condition which method comprises administering to a subject suffering from said condition a therapeutically effective amount of amorphous lisinopril or a product comprising amorphous lisinopril. In a further embodiment a therapeutically effective amount of a composition comprising amorphous lisinopril is administered to the subject.

The invention also provides amorphous lisinopril for use in treating hypertension, congestive heart failure, acute myocardial infarction and in renal and retinal complications of diabetes mellitus.

The invention also provides the use of amorphous lisinopril in treating hypertension, congestive heart failure, acute myocardial infarction and in renal and retinal complications of diabetes mellitus.

Any suitable route of administration may be employed for providing the patient with an effective dosage of drug comprising amorphous lisinopril according to the invention. For example, peroral or parenteral formulations and the like may be employed. Dosage forms include capsules, tablets, dispersions, suspensions and the like, e.g. enteric-coated capsules and/or tablets, capsules and/or tablets containing enteric-coated pellets of lisinopril. In all dosage forms amorphous lisinopril can be admixtured with other suitable constituents. The preferred route of administration is peroral using fast melt tablets.

The compositions of the invention comprise the compound of the invention. The compositions may be conveniently presented in unit dosage forms, and prepared by any methods known in the art of pharmacy.

In view of the enhanced solubility that amorphous lisinopril has compared to crystalline lisinopril, compositions wherein some, but preferably a substantial amount, of the total amount of the lisinopril is amorphous (i.e. >20%), can be prepared as a 'fast melt' tablet and/or formulation.

A fast melt tablet is defined as a tablet dosage form for oral use that disintegrates in the mouth within approximately one minute. Chewing or water is not needed for disintegration. Should the drug and tablet excipients be sufficiently soluble, the tablet dissolves to a complete solution before the patient swallows.

Several advantages of fast melt tablets over conventional oral tablets and liquids may exist. Patient compliance may improve because of ease of swallowing, lack of need for water, and taste-masking and improved accuracy of dosage. Patient populations that may benefit the most include geriatric patients, paediatric patients and patient who cannot swallow or have difficulty in swallowing. A fast melt tablet would also benefit patients with congestive heart failure who tend to retain fluid, and therefore are treated with fluid intake restriction. The fluid used to take their medications are included in the amount of fluid that they are prescribed per day (which may be as little as 500 ml), so a fast melt tablet that can be taken without fluid would benefit these patients.

Fast melt tablets are manufactured by a variety of tablet technologies including wet granulation, direct compression and freeze-drying (see for example: Corveleyn and Remon, International Journal of Pharmaceutics, (1997) 152:215–225).

For a general review on fast melt technology please consult, Habib et al., (Critical Reviews in Therapeutic Drug Carrier Systems, 17(1):61–72, 2000).

According to a further aspect of the invention there is provided a fast melt tablet formulation comprising amorphous lisinopril.

Crystalline lisinopril dihydrate is soluble in water and should go into solution in the gastrointestinal tract rapidly after ingestion. This is demonstrated by the dissolution of the current marketed Zestril® tablets in which typically greater than 90% of the dose is dissolved within 15 minutes. Once in solution, absorption is limited by the physicochemical characteristics of the compound, its ability to cross the gastrointestinal mucosa and enter into the blood stream and transit time of the gut. A form that would go into solution more rapidly would only affect the first step however. Thus, despite the enhanced solubility that a lisinopril formulation comprising amorphous form would likely have, because solubility is not a limiting step in the rate and extent of absorption of lisinopril, it is unlikely that this would affect the bioavailability or the clinical benefits of lisinopril.

In the practice of the invention, the most suitable route of administration as well as the magnitude of a therapeutic dose of amorphous lisinopril in any given case will depend on the nature and severity of the disease to be treated. The dose, and dose frequency, may also vary according to the age, body weight, and response of the individual patient.

In general, a suitable oral dosage form may cover a dose range from 0.5 mg to 150 mg total daily dose, administered in one single dose or equally divided doses. A preferred dosage range is from 1 mg to 60 mg.

Combination therapies comprising amorphous lisinopril and other active ingredients in separate dosage forms, or in one fixed dosage form, may also be used. Examples of such active ingredients include anti-bacterial compounds, non-steroidal anti-inflammatory agents, antacid agents, alginates, prokinetic agents, other antihypertensive agents, diuretics, digitalis, thrombolytics, aspirin and beta-blockers.

The invention is further illustrated, but in no way limited, by the following examples and figures in which.

EXAMPLES

Example 1

Preparation of Amorphous Lisinopril

This process of making stable amorphous lisinopril was discovered by accident since the initial intention was to produce a methanol solvate by this process.

Crystalline lisinopril dihydrate (423.5 mg), prepared according to standard methodology, in a 20 ml vial was placed in an oven at 120° C. having a vacuum 800 mbar for 2 hours to remove water of crystallisation. Immediately on opening the oven 20 ml of methanol was added to the hot samples. The methanol was evaporated down to 5 ml on a hot plate and then allowed to cool to 25° C. Sufficient acetone was added as an antisolvent to precipitate a white solid. This was filtered and dried in an oven at 60° C. for 1 hour.

The product was tested via HPLC to confirm that it was lisinopril.

Example 2

Characterization of Amorphous Lisinopril and Crystalline Lisinopril Using X-ray Powder Diffraction X-ray diffraction analysis was performed according to standard methods which can be found in e.g. Bunn, C. W. (1948), Chemical Crystallography, Clarendon Press, London; or Kiug, H. P. & Alexander, L. E. (1974), X-Ray Diffraction Procedures, John Wiley and Sons, New York.

Approximately 700 mg of sample was tested.

Figure 1:
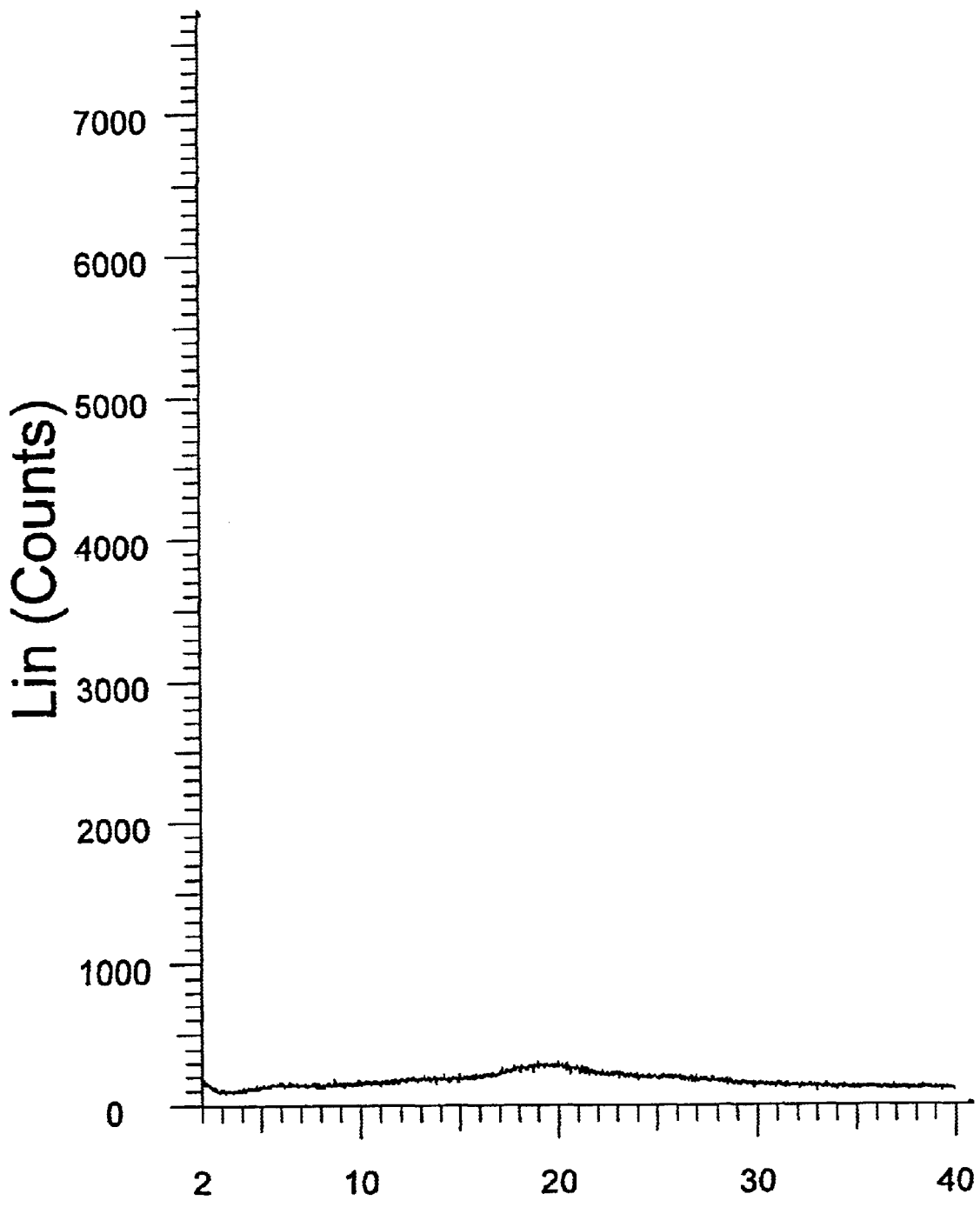
FIG. 1 is an X-ray powder diffractogram of amorphous lisinopril.

The lisinopril produced according to Example 1 forms a surprisingly stable amorphous form which by x-ray powder diffraction (XRPD) giving a characteristic amorphous halo due to a lack of long range order and showing an absence of discernible diffraction peaks (FIG. 1).

Figure 2:
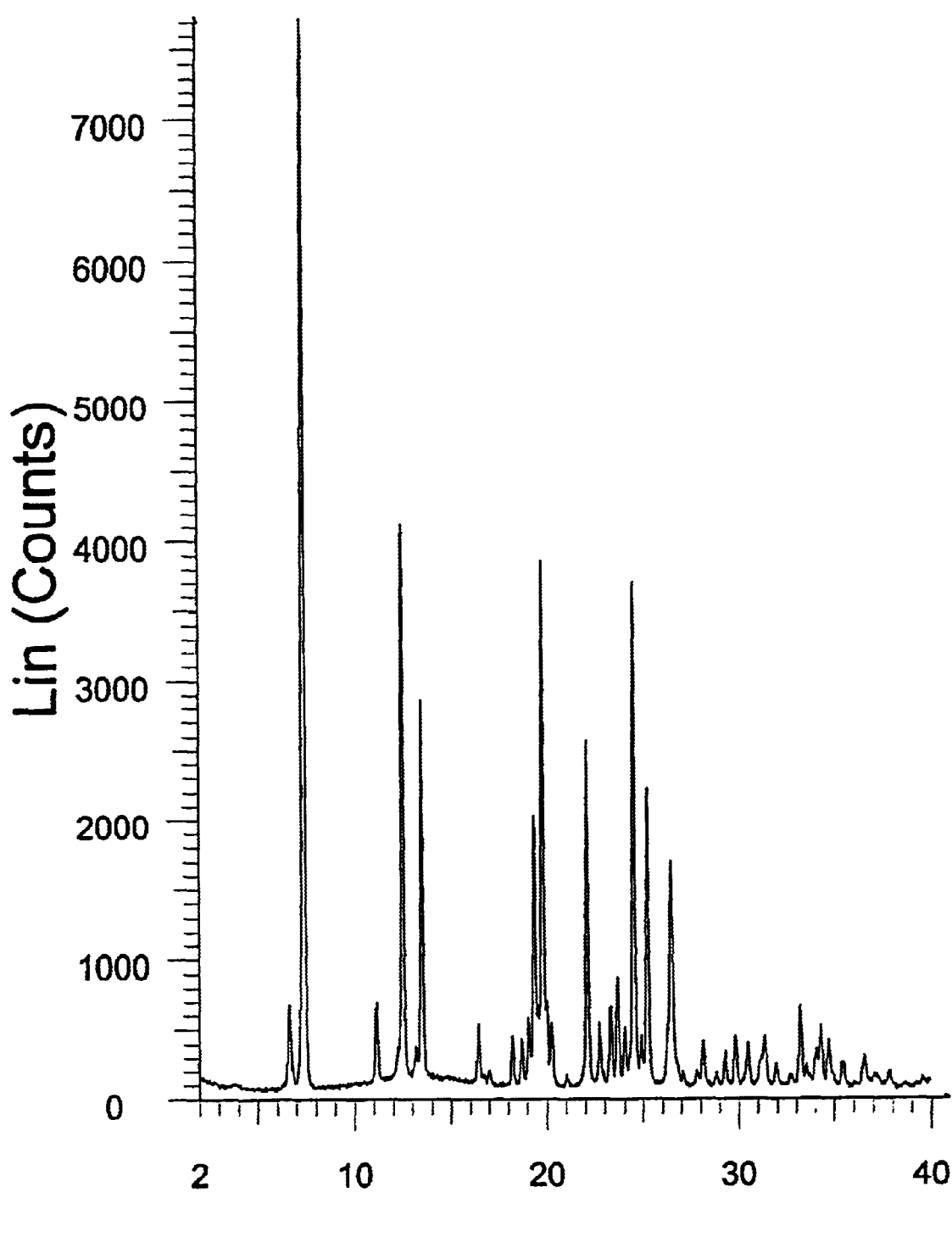
FIG. 2 is an X-ray powder diffractogram of crystalline lisinopril.

In contrast the XRPD pattern of crystalline lisinopril dihydrate shows a large number of peaks over the same two theta scale (FIG. 2) showing that it is crystalline.

Example 3

Amorphous Lisinopril Stability Test

Figure 3:
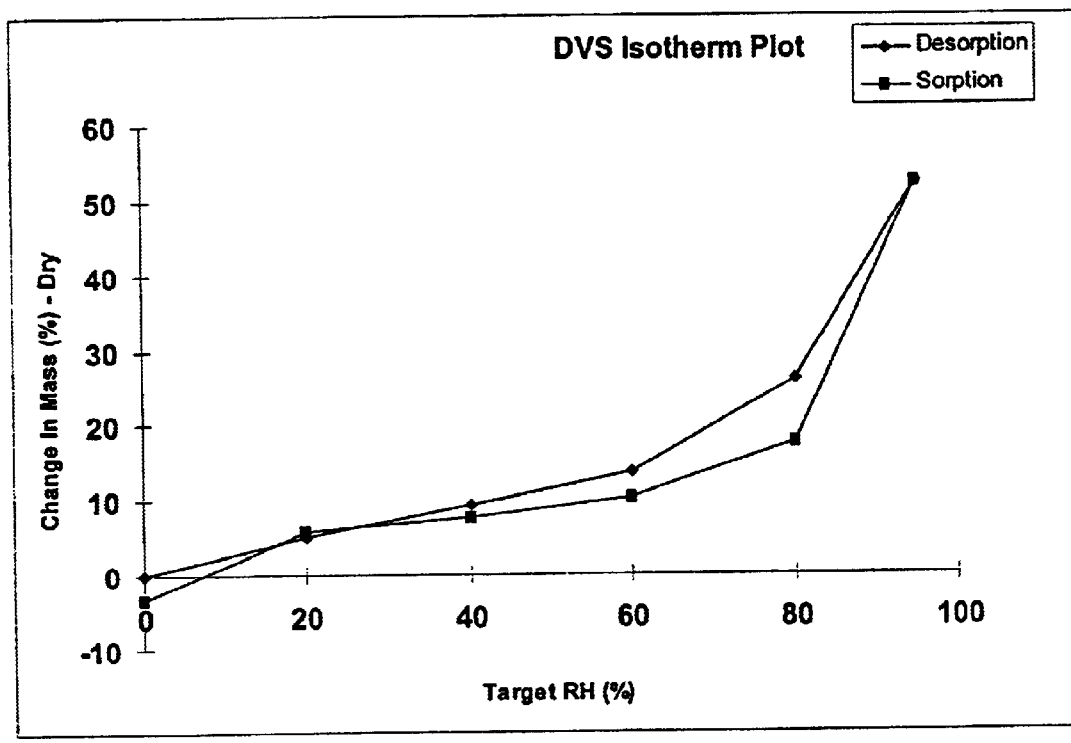
FIG. 3 is a Dynamic vapour sorption (DVS) isotherm of amorphous lisinopril.

Dynamic vapour sorption (DVS) was determined on approximately 5–50 mg amorphous lisinopril sample in order to provide further information on the physical stability according to the method described in Ticehurst, et al., (International Journal of Pharmaceutics 193:247–259, 2000). The results are shown in FIG. 3. With amorphous lisinopril, no expulsion of absorbed water due to recrystallisation was observed during the first sorption process (Cycle 1Sorp). This is in contrast to amorphous revatropate hydrobromide (Ticehurst, et al., International Journal of Pharmaceutics 193:247–259, 2000) which showed increase in water content up to 29% RH followed by a rapid expulsion of water due to crystallisation. The fact that this did not occur with amorphous lisinopril suggests that the amorphous lisinopril material is physically stable to the effects of water to initiate crystallisation.

Example 4

Characterisation of Amorphous Lisinopril by DSC, TGA and TMA

Differential Scanning Calorimetry (DSC) was performed on approximately 0.5–3 mg sample, using a Mettler DSC820 instrument, according to standard methods, for example those described in Hohne et al. (1996) *Differential scanning Calorimetry*, Springer, Berlin. The amorphous lisinopril prepared according to example 1, showed loss of water at approximately 110° C., this was determined by Thermogravimetric analysis (TGA) using a Mettler Toledo TGA851 instrument, to be water loss of approximately 9% (approx. 2–20 mg of sample was tested for this). The DSC also showed an anomalous endotherm at 125° C. equivalent to the glass transition temperature ($T_g$) for dry amorphous lisinopril. In addition the DSC showed an absence of any thermal event associated with melting thus providing further evidence that the material is amorphous.

Thermal Mechanical Analysis (TMA) using the method disclosed in Widmann and Riesen (*Thermal Analysis: Terms, Methods, Aplications* (1987) Heidelberg Huthag, Germany) and a Mettler Toledo TMA40 instrument, was used to determine the glass transition point of amorphous lisinopril more accurately. The method involves compressing 140 mg of material in a punch and die (3 mm) to 2 KN. The compressed pellet was then placed on the TMA and the 1.1 mm probe placed on the top face. A heating rate of 10° C./min was used and the sample was heated from 30–160° C. This gave a glass transition temperature of the amorphous lisinopril of 129° C. This indicates that amorphous lisinopril will not crystallise at ambient temperatures and humidities inferring sufficient shelf life stability.

Example 5

Characterisation of Amorphous Lisinopril and Crystalline Lisinopril Using $^{13}C$ Solid State NMR $^{13}C$ Solid state NMR was performed according to standard methods, for example those found in *Nuclear Magnetic*

*resonance Spectroscopy*, R K Harris, Longman (1987), p. 155. i.e. spectra acquired with cross polarization, magic angle spinning and high power proton decoupling.

Approximately 200 mg of sample prepared in Example 1 was tested.

From the solid state NMR spectra of amorphous (FIG. 4) compared with that of crystalline lisinopril dihydrate (FIG. 5) the differences can be clearly seen. In the case of amorphous, there is a broadening of the peaks in the spectra by $^{13}$C solid state NMR, indicative of amorphous material due to a lack of long range order. In contrast the $^{13}$C solid state NMR spectra of crystalline lisinopril dihydrate has sharp, well defined peaks (FIG. 5) showing that it is crystalline.

Figure 4:
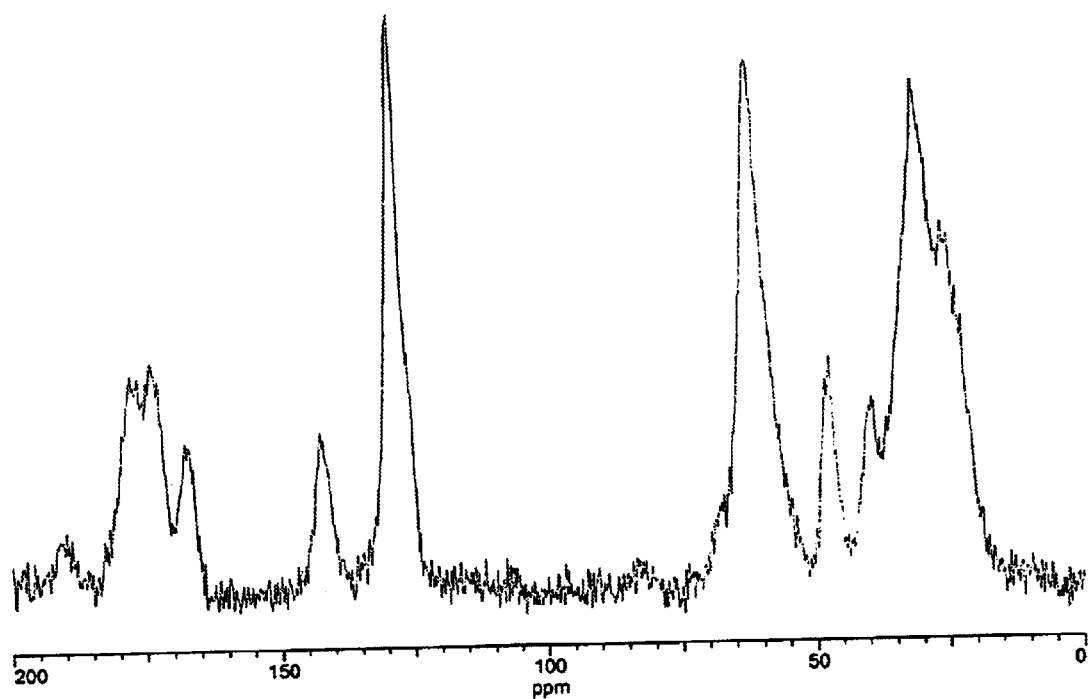
FIG. 4 is a solid state nuclear magnetic resonance (ssNMR) spectrum of amorphous lisinopril.
Figure 5:
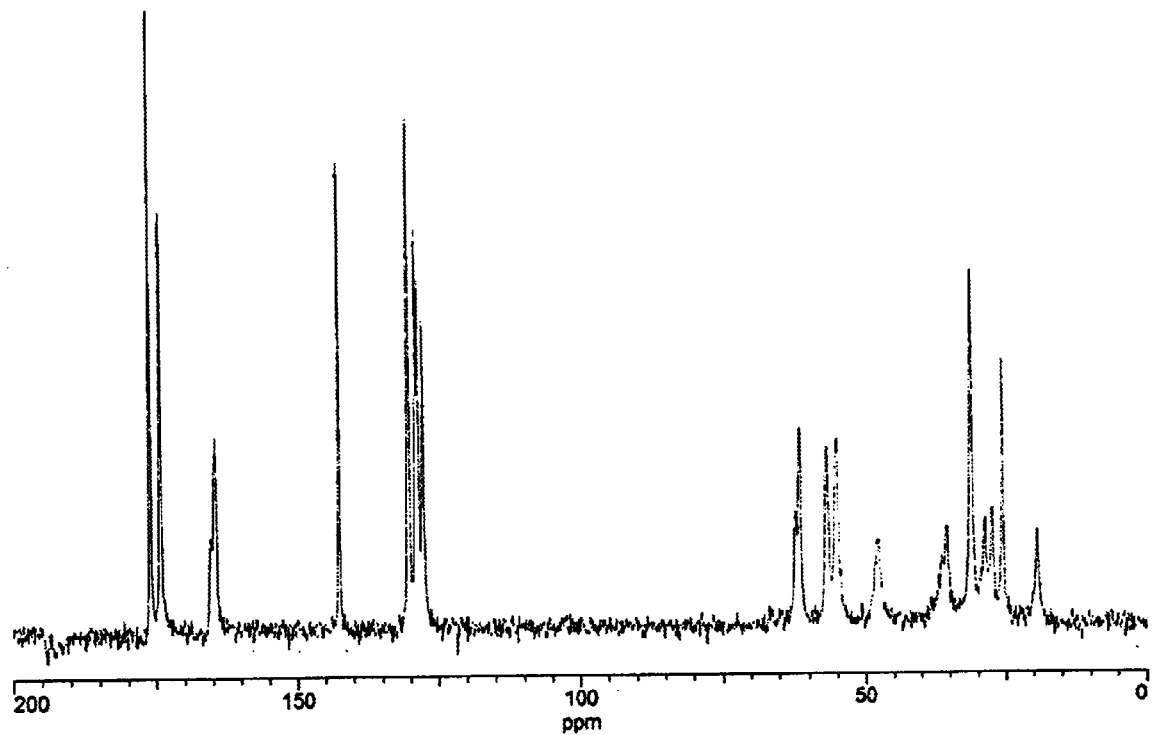
FIG. 5 is an ssNMR spectrum of crystalline lisinopril dihydrate.
Figure 6:
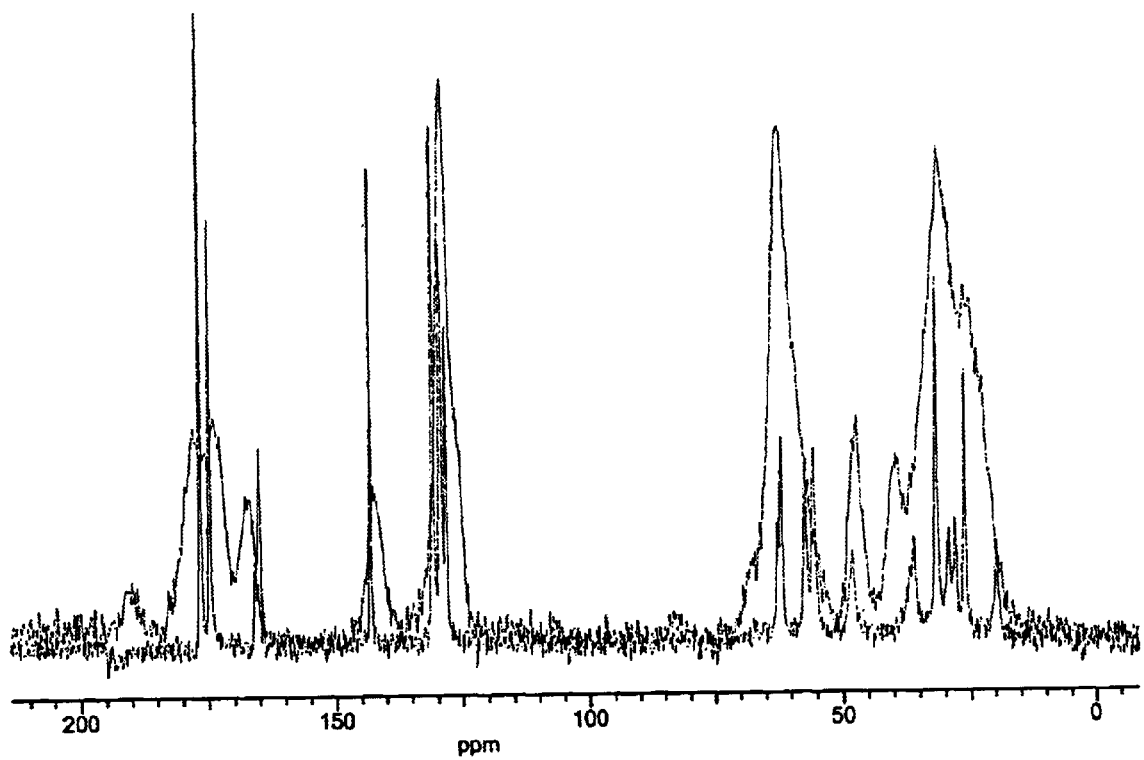
FIG. 6 is an ssNMR spectrum overlay of amorphous and crystalline lisinopril.

FIG. 6 is an overlay of FIGS. 4 and 5.

Example 6

Solubility Determination

Standard dihydrate crystalline lisinopril was tested alongside the amorphous lisinopril made following the process outlined in Example 1.

Solubility was assessed using known quantities (approx 1 mg) and titrating small volumes (2–40 microliters) of deionised water and assessed visually. The data given are ranges. The lower limit represents soluble and upper limit the presence of undissolved material.

| Sample | solubility (mg/ml) | Reference solubility (mg/ml) |
| --- | --- | --- |
| Dihydrate | 60–65 | 97[1] |
| Amorphous | 900–1250 | — |

[1]Ip et al., In Analytical profiles of drug substances and excipients (Ed. Brittain, H. G.), Academic Press Inc., San Diego, USA, (1992) 21:233–276.

This indicates that the amorphous form of lisinopril is at least 15-fold more soluble than crystalline lisinopril. Drug forms with such enhanced solubility are particularly useful in fast melt formulations.

Example 7

Other Methods for Making Amorphous Lisinopril

A) 5 g anhydrous lisinopril was dissolved in 50 ml water. This aqueous solution of lisinopril was added to toluene (approximately 500 ml) and the water removed under vacuum by azeotropic distillation. When the volume was reduced to 100–150 ml, another portion of toluene was added and the procedure repeated. The procedure was repeated a third time (further portions of toluene could have been used if desired since lisinopril is insoluble in toluene). Amorphous lisinopril was precipitated and collected simply by decanting off the solvent.

B) As for A) above, except that the antisolvent toluene was replaced with chlorobenzene.

C) A sample of amorphous lisinopril was prepared by freeze-drying an aqueous solution. An aqueous solution of lisinopril was frozen and the water removed from the frozen sample under a vacuum of about 0.5 mm Hg.

Each of these methods generated amorphous product.

I claim:

1. Amorphous lisinopril.
2. Lisinopril comprising at least 1%, by weight, of amorphous lisinopril according to claim 1.
3. Lisinopril according to claim 2, wherein the amorphous lisinopril provides an X-ray powder diffraction pattern containing one or more broad diffuse halos.
4. Lisinopril according to claim 2, wherein the X-ray powder diffraction pattern also lacks any discernible peaks.
5. Lisinopril according to claim 2, wherein the amorphous lisinopril has a glass transition point (Tg) when dry, measured by Thermal Mechanical Analysis (TMA), of 100° C. or more.
6. Lisinopril according to claim 2, wherein the amorphous lisinopril has a glass transition point (Tg) when dry, measured by Thermal Mechanical Analysis (TMA), of 120° C. or more.
7. Lisinopril according to claim 2, wherein the amorphous lisinopril provides an X-ray powder diffraction pattern containing one or more broad diffuse halos and when dry, a Tg measured by TMA, of at least 100° C.
8. Lisinoprfl comprising at least 5%, by weight, of amorphous lisinopril according to claim 1.
9. Lisinopril according to claim 8, wherein the amorphous lisinopril provides an X-ray powder diffraction pattern containing one or more broad diffuse halos.
10. Lisinopril according to claim 8, wherein the X-ray powder diffraction pattern also lacks any discernible peaks.
11. Lisinopril according to claim 8, wherein the amorphous lisinopril has a glass transition point (Tg) when dry, measured by Thermal Mechanical Analysis (TMA), of 100° C. or more.
12. Lisinopril according to claim 8, wherein the amorphous lisinopril has a glass transition point (Tg) when dry, measured by Thermal Mechanical Analysis (TMA), of 120° C. or more.
13. Lisinopril according to claim 8, wherein the amorphous lisinopril provides an X-ray powder diffraction pattern containing one or more broad diffuse halos and when dry, a Tg measured by TMA, of at least 100° C.
14. Lisinopril comprising at least 50%, by weight, of amorphous lisinopril according to claim 1.
15. Lisinopril according to claim 14, wherein the amorphous lisinopril provides an X-ray powder diffraction pattern containing one or more broad diffuse halos.
16. Lisinopril according to claim 14, wherein the X-ray powder diffraction pattern also lacks any discernible peaks.
17. Lisinopril according to claim 14, wherein the amorphous lisinopril has a glass transition point (Tg) when dry, measured by Thermal Mechanical Analysis (TMA), of 100° C. or more.
18. Lisinopril according to claim 14, wherein the amorphous lisinopril has a glass transition point (Tg) when dry, measured by Thermal Mechanical Analysis (TMA), of 120° C. or more.
19. Lisinopril according to claim 14, wherein the amorphous lisinoprl provides an X-ray powder diffraction pattern containing one or more broad diffuse halos and when dry, a Tg measured by TMA, of at least 100° C.
20. A pharmaceutical composition comprising amorphous lisinopril according to any one of claims 1–19 in admixture with a pharmaceutically-acceptable carrier, diluent or excipient.
21. The composition according to claim 20, wherein the composition is in the form of a fast melt tablet.
22. A fast melt tablet comprising lisinopril according to any one of claims 1–19.

* * * * *

UNITED STATES PATENT AND TRADEMARK OFFICE
CERTIFICATE OF CORRECTION

| | | |
|---|---|---|
| PATENT NO. | : 6,627,760 B1 | Page 1 of 1 |
| APPLICATION NO. | : 09/891190 | |
| DATED | : September 30, 2003 | |
| INVENTOR(S) | : Ronald John Roberts | |

It is certified that error appears in the above-identified patent and that said Letters Patent is hereby corrected as shown below:

Col. 12, line 4 (claim 4)
"claim 2" should read --claim 3--.

Col. 12, line 24 (claim 10)
"claim 8" should read --claim 9--.

Col. 12, line 44 (claim 16)
"claim 14" should read --claim 15--.

Signed and Sealed this

Fifteenth Day of January, 2008

JON W. DUDAS
*Director of the United States Patent and Trademark Office*